United States Patent
Seguin

(10) Patent No.: US 9,815,783 B2
(45) Date of Patent: Nov. 14, 2017

(54) (3-ALKYLTHIO)PROPENOIC ACID-DERIVED COMPOUNDS AND THEIR APPLICATION IN COSMETICS

(71) Applicant: EXSYMOL, Monaco (MC)

(72) Inventor: Marie-Christine Seguin, Monaco (MC)

(73) Assignee: EXSYMOL, Monaco (MC)

( * ) Notice: Subject to any disclaimer, the term of this patent is extended or adjusted under 35 U.S.C. 154(b) by 0 days.

(21) Appl. No.: 15/179,382

(22) Filed: Jun. 10, 2016

(65) Prior Publication Data

US 2016/0362364 A1    Dec. 15, 2016

(30) Foreign Application Priority Data

Jun. 12, 2015 (FR) ..................... 15 55368

(51) Int. Cl.
| | |
|---|---|
| A61K 8/46 | (2006.01) |
| C07C 323/41 | (2006.01) |
| A61Q 17/04 | (2006.01) |
| C07C 317/44 | (2006.01) |
| C07C 323/60 | (2006.01) |
| A61K 8/19 | (2006.01) |
| A61K 8/34 | (2006.01) |
| A61K 8/36 | (2006.01) |
| A61K 8/37 | (2006.01) |
| A61K 8/41 | (2006.01) |
| A61K 8/49 | (2006.01) |
| A61K 8/60 | (2006.01) |
| A61K 8/73 | (2006.01) |
| A61K 8/81 | (2006.01) |
| A61K 8/92 | (2006.01) |

(52) U.S. Cl.
CPC .............. *C07C 323/41* (2013.01); *A61K 8/19* (2013.01); *A61K 8/34* (2013.01); *A61K 8/342* (2013.01); *A61K 8/36* (2013.01); *A61K 8/37* (2013.01); *A61K 8/41* (2013.01); *A61K 8/46* (2013.01); *A61K 8/4973* (2013.01); *A61K 8/608* (2013.01); *A61K 8/73* (2013.01); *A61K 8/8111* (2013.01); *A61K 8/922* (2013.01); *A61Q 17/04* (2013.01); *C07C 317/44* (2013.01); *C07C 323/60* (2013.01)

(58) Field of Classification Search
CPC ...................................................... A61K 8/46
See application file for complete search history.

(56) References Cited

U.S. PATENT DOCUMENTS

| | | | |
|---|---|---|---|
| 3,914,301 A | 10/1975 | Miller et al. | |
| 5,300,672 A | 4/1994 | Weinstein et al. | |
| 5,464,832 A | 11/1995 | Osei-Gyimah et al. | |
| 2009/0220442 A1* | 9/2009 | Brillouet | A61K 8/35 424/60 |

FOREIGN PATENT DOCUMENTS

EP    0410726    1/1991

OTHER PUBLICATIONS

Hinterberger et al (Synthesis of amides from Glycosmis species: Methylthiopropenoic acid, methylsulfonylpropenoic acid, thiocarbamic acid S-methyl ester, and senecioic acid amides, Tetrahedron, vol. 54, Issues 3-4, Jan. 15, 1998, pp. 487-496).*
Preliminary Search Report issued in the French Application No. 1555368 dated Apr. 1, 2016 (1 page).
Tu et al.: "Chemical Constituents and Bioactivities of Clinacanthus nutans Aerial Parts"; Molecules, 2014, vol. 19, No. 12, pp. 20383-20390.
Pacher et al.: "Alcoholysis of Naturally Occurring Imides: Misleading Interpretation of Antifungal Activities"; Journal of Natural Products, vol. 73, 2010, pp. 1389-1393.
Crow et al: "Isothiazole Chemistry VI. Reactions of Carbanions with N-Ethyl-3-Isothiazolone"; Australian Journal of Chemistry, 1969, vol. 22, pp. 765-774.
Beck et al.: "Study of the photochemical behaviour of sunscreens—benzylidene camphor and derivatives"; International Journal of Comestic Science, Kluwer Academic Publishers, 1981, vol. 3 pp. 139-152.
Ichihashi et al.: "UV-induced skin damage"; Toxicology, 2003, vol. 189, pp. 21-39.
Barresi et al.: "Increased Sensitivity of Histidinemic Mice to UVB Radiation Suggests a Crucial Role of Endogenous Urocanic Acid in Photoprotection"; Journal of Investigative Dermatology, 2011, vol. 131, pp. 188-194.
Lacour et al.: "Photoprotection naturelle, photoprotection exteme (topique et vestimentaire)"; Annales de Dermatologie et Venereologie, 2007, vol. 134, pp. 18-24.
Rai et al.: "Update on Photoprotection"; Indian Journal of Dermatology, 2012, vol. 57.5, pp. 335-342.
Bruge et al: "Prevention of UVA-Induced Oxidative Damage in Human Dermal Fibroblasts by New UV Filters, Assessed Using a Novel In Vitro Experimental System"; PLOS ONE, 2014, vol. 9, e83401, pp. 1-11.
Uther et al.: "Coupled exposure to ingredients of cosmetic products: III. Ultraviolet filters"; Contact Dermatitis, 2014, vol. 71, pp. 162-169.
Matsui et al.: "Non-Sunscreen Photoprotection: Antioxidants Add Value to a Sunscreen"; Journal of Investigative Dermatology Symposium Proceedings, 2009, vol. 14, pp. 56-59.

(Continued)

*Primary Examiner* — Benjamin Packard
(74) *Attorney, Agent, or Firm* — Hamre, Schumann, Mueller & Larson, P.C.

(57) ABSTRACT

The present invention relates to compounds of general formula (I):

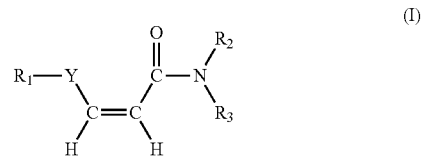

wherein Y, $R_1$, $R_2$ and $R_3$ are as defined in the specification.
The invention also relates to cosmetic or dermocosmetic composition containing such compounds.
The compounds according to the invention are useful as photoprotective agents.

19 Claims, No Drawings

(56) References Cited

OTHER PUBLICATIONS

Liebel et al.:"Irradiation of Skin with Visible Light Induces Reactive Oxygen Species and Matrix-Degrading Enzymes"; Journal of Investigative Dermatology, 2012, vol. 132, pp. 1901-1907.

Schroeder et al.: "The role of near infrared radiation in photoaging of the skin"; Experimental Gerontology, 2008, vol. 43, pp. 629-632.

Ikegami et al.: "Synthesis of Entadamide A and Entadamide B Isolated from Entada phaseoloides and Their Inhibitory Effects on 5-Lipoxygenase"; Chem. Pharm. Bull., 1989, vol. 37, pp. 1932-1933.

De Medeiros et al.: "The Synthesis and Absolute Configuration of the Novel Ichthyotoxic Diacylglycerols, Umbraculumin A and Unbraculumin C"; J. Chem. Soc. Perking Trans. I, 1991, No. 11, pp. 2725-2730.

McLoone et al.: "An Action Spectrum for the Production of cis-Urocanic Acid in Human Skin In Vivo"; Journal of Investigative Dermatology, 2005, Vol. 124, pp. 1071-1074.

Gibbs et al.: "Urocanic Acid in the Skin: A Mixed Blessing?"; Journal of Investigative Dermatology, 2011, vol. 131, pp. 14-17.

Poon et al.: "Prevention of Immunosuppression by Sunscreens in Humans Is Unrelated to Protection from Erythema and Dependent on Protection from Ultraviolet A in the Face of Constant Ultraviolet B Protection", Journal of Investigative Dermatology, 2003, Vo. 121, 184-190.

Wolf et al.: "Immune Protection Factors of Chemical Sunscreens Measured in the Local Contact Hypersensitivity Model in Humans"; Journal of Investigative Dermatology, 2003, vol. 121, pp. 1080-1087.

Beck et al.: "Study of the photochemical behaviour of sunscreens—benzylidene camphor and derivative"; International Journal of Cosmetic Science, 1981, vol. 3, pp. 139-152.

Hurks et al.: "Differential Effects of Sunscreens on UVB-Induced Immunomodulation in Humans"; Journal of Investigative Dermatology, 1997, vol. 109, pp. 699-703.

Finlay-Jones et al.: "Photoprotection: sunscreens and the immunomodulatory effects of UV irradiation"; 1998, vol. 422, pp. 155-159.

\* cited by examiner

(3-ALKYLTHIO)PROPENOIC ACID-DERIVED COMPOUNDS AND THEIR APPLICATION IN COSMETICS

FIELD OF THE INVENTION

The object of the present invention is a family of conjugated compounds derived from 3-(alkylthio)propenoic acid, as well as their uses in cosmetics as photoprotective agent of sun radiations. The invention also relates to cosmetic compositions intended for photoprotection of skin or appendages.

BACKGROUND OF THE INVENTION

Alongside of its beneficial effects (support to vitamin D and melatonin production, antidepressant, well-being, etc), sun also causes short- and long-term misdeeds on skin: erythema, tissue premature aging, photodermatoses, carcinoma, melanoma (Ichihashi M. et al., Toxicology, 2003, vol. 189, pp. 21-39). And among the various families of rays that reach the earth's surface, ultraviolet rays limited to ultraviolet-A (λ 320-400 nm, UV-A) or ultraviolet-B (λ 290-320 nm, UV-B) radiations have been identified as being the source of such misdeeds.

Skin has however intrinsic defense systems that enable it to fight against sun damages. Thus as a result of sun radiation, a so-called natural or internal photoprotection already expresses therein, which is ensured by a production of photoprotective melanin pigments, or else by a thickening of stratum corneum with a greater number of keratinocyte layers in epidermis. Trans-urocanic acid which is a histidine metabolite and is present in high concentration in the upper layers of epidermis and particularly in stratum corneum, is also involved in this natural photoprotection by expressing an endogenous protective role against the harmful action of UV-B (Barresi C. et al., J. Invest. Dermatol. 2011, vol. 131, pp. 188-194).

Skin protection against sun radiation can also be induced extrinsically (Lacour et al., Annales de Dermatologie et Vénéreologie, 2007, vol. 134, pp. 18-24). In general, such a photoprotection, that can be qualified as artificial compared to natural photoprotection, is ensured by external means comprising the topical application of photoprotective cosmetic products, in addition to covering clothing. These products or preparations usually contain protective substances dissolved or dispersed in an excipient and that can be classified into three broad categories: sunscreens whose action is to reflect all sun radiations and therefore to prevent their penetration into skin; filters whose action is to absorb a part of sun radiations, usually ultraviolet-A (320-400 nm) and B (290-320 nm) rays and then to release the photon energy absorbed by heat exchange with skin; and finally photoprotective agents which are said active compared to sunscreens and filters and which are usually substances capable of trapping reactive oxygen species ("ROS") formed when radiations are absorbed by molecules naturally present in skin (photo-sensitization mechanism).

Such topical preparations are generally characterized by a sun protection factor ("SPF"), which is an indicator of the protection level against erythema (sunburn) and which is adapted to sunlight conditions and to peculiar skin phototypes. For sun protection formulations with high SPF, sunscreens and filters are associated.

Sunscreens in such preparations are mostly inert substances of mineral origin (powders: zinc oxide, titanium dioxide, etc). Their use in sunscreen formulations remains however cumbersome with the appearance of white marks when they are applied. A presentation under the form of nanoparticles improves the marketing of these sunscreens, although their safety in this form has been challenged for a few years with a potential risk to penetrate skin.

Organic chemical filters are generally of synthetic origin, or of natural origin when they are oils or extracts derived from plants. Their efficiency consists of an absorbing effect of ultraviolet light due to the structural presence of chromophore groups capable of absorbing, then dissipating light rays with specific wavelength. The chromophore groups in these chemical filters are almost systematically compounds bearing a mono- or polycyclic aromatic ring (phenyl, benzyl, benzylidene, benzoyl, naphthyl, anthracenyl, etc) which is conjugated to carbonyl groups or aliphatic unsaturated systems for a greater delocalization of electrons under the effect of absorbed radiations (excited state), before returning to a stable state with dissipation of the received photon energy and/or re-emission of a less dangerous radiation (for example infrared).

Thus, there may be mentioned among these chromophore chemical filters which belong to the state of the art (R. Rai and al., Indian J. Dermatol., 2012, vol. 57(5), pp. 335-342) and are commercially available, the following compounds whose absorption spectrum is rather UV-B-specific:
  para-aminobenzoic acid (PABA) ester derivatives, such as 2-ethylhexyl-4-dimethylaminobenzoate (padimate O),
  methoxycinnamic acid derivatives such as octyl methoxycinnamate (octinoxate or OMC) and 2-ethoxyethylmethoxycinnamate (cinoxate),
  salicylic acid derivatives such as ethylhexylsalicylate (octisalate) and trolamine salicylate,
  2-ethylhexyl-2-cyano-3,3-diphenyl-2-propenoate (octocrylene),
  phenyl-benzimidazole sulfonic acid (ensulizole).

There may also be mentioned the following compounds whose absorption spectrum is rather UV-A-specific:
  dibenzoylmethane derivatives such as butyl methoxydibenzoylmethane (avobenzone),
  terephtalidene dicamphor sulfonic acid (ecamsule or Mexoryl SX®).

There may finally be mentioned the following compounds whose absorption spectrum is wider (UV-B and UV-A radiations):
  benzophenones such as benzophenone-3 (oxybenzone) and benzophenone-8 (dioxybenzone),
  hydroxybenzotriazoles derivatives,
  new triazines such as benzoxazines (Bruge and al., PLoS ONE, 2014, 9, e83401.).

For many of these organic filters that are primarily chosen for physico-chemical criteria (SPF, absorption spectrum, persistence to skin surface), it emerges beyond some potential allergic disorders (contact allergies, photo-allergies, itching) yet reported over the last few years (Uther W. and al., Contact Dermatitis, 2014, vol. 71, pp. 162-9), that the photochemical innocuousness of these chromophores agents, especially of their degradation products such as the photo-isomerization products, is not always indicated.

More recently, other protective strategies have been developed with the introduction of active agents in sun formulations, such as DNA repair enzymes and above all antioxidants like vitamins C and E, or polyphenols (MS Matsui and al., J. Invest. Dermatol., 2009, vol. 14, pp. 56-59). The interest in this strategy has been reinforced with recent evidence of the capacity of visible (400-700 nm) and near infrared (700-1440 nm) radiations to induce the formation of ROS in the skin (F Liebel and al, J. Invest Dermatol, 2012, vol 132, pp. 1901-1907; Schroeder P. and al., Exp Gerontol, 2008, vol 43, pp. 629-632). Once again, the inclusion of such active ingredients in topical formulations is not without raising troubles: lack of stability, cost, and above all the formation, when in contact with oxygen or its reactive species, of by-products whose toxicology is often unknown.

Accordingly with regard to these different facts, the applicant focused on identifying new photoprotective compounds for topical cosmetic purposes and with a broad-spectrum protection against sun radiation, along with a concomitant objective to design products that do not form degradation or photo-conversion by-products which could be poorly tolerated by skin. Ensuring evidence of the innocuousness of substances of interest, but also of the innocuousness of reaction by-products resulting from the targeted cosmetic activity, has become of high priority in the cosmetic or dermocosmetic industry.

BRIEF SUMMARY OF THE INVENTION

In order to achieve these objectives, the applicant was originally interested in a sulfur-containing antioxidant compound, 3-methylthiopropenoic acid (TMPA) which has been identified in certain plants under the form of conjugates like the amide conjugate of trans-3-methylthiopropenoic acid (E-TMPA) with ethanolamine. This conjugate was isolated from seeds of leguminous plants with a reported anti-inflammatory potential (Ikegami F. et al., Chem. Pharm. Bull., 1989, Vol. 37, pp. 1932-1933).

Then in the course of a structure-activity research to optimize the antioxidant power of TMPA conjugates, the applicant has discovered that a panel of original amide conjugates obtained from TMPA unnatural stereoisomer, the cis-3-methylthiopropenoic acid (Z-TMPA) prepared stereoselectively (Faria de Medeiros E. et al., J. Chem. Soc., Perkin Trans I, 1991 No. 11, pp. 27525-2730), displayed an unexpected ability to absorb so efficiently the UV-B radiation and to dissipate the captured energy by isomerization to produce its trans-configuration stereoisomer. Subsequently, the applicant observed that this feature came with the property to oppose the photo-induced endogenous isomerization of the above-mentioned natural photoprotector, namely the trans-urocanic acid. This has the advantage to preserve the protective activity of the skin intrinsic defense system, but above all to oppose the negative effects linked to the photo-isomerization of trans-urocanic acid. Indeed, it is well established nowadays that its behavior of "natural sunscreen" (absorption of light energy) leads trans-urocanic acid (or "E-UCA") to be converted to cis-urocanic acid (or "Z-UCA") to which is unfavorably attributed a pro-oxidant behavior that is responsible for intracellular damages and in particular for DNA damages, and which behavior negates the benefits of E-UCA, (Mc Loone P. et al., J. Invest. Dermatol, 2005, vol. 124, pp. 1071-1074; Gibbs N K et al, J. Invest Dermatol, 2011, vol. 131, pp. 14-17 and quoted references). Z-UCA is also unfavorably involved in the suppressive effect of ultraviolet radiation on the immune system. Such a "LV-induced immunosuppression" results, at skin level, in a deficiency of the immune response to sensitizing agents, as well as in an increased sensitivity against infections and an increased risk of skin cancers (Poon T. S. C. et al., J. Invest. Dermatol., 2003, vol. 121, pp. 184-190). Fighting against the ultraviolet radiation-induced immunosuppression is also nowadays another major objective in photoprotection, and for that purpose an immune protection factor ("IPF") was defined (Wolf P. et al., J. Invest. Dermatol., 2003, vol. 121, pp. 1080-1087) which is mentioned for certain sun protection formulations.

Overall, the identified panel of original amide-type conjugates derived from cis-3-methylthiopropenoic acid achieves the objective to safely provide a broad protection against sun radiation, thanks to:

an antioxidant power which allows them to oppose the oxidative stress generated by photo-sensitization reactions involving endogenous chromophores (porphyrins, quinones, flavins, etc) and radiations as various as ultraviolet, visible and near infrared. Such an effect is thus able to oppose the formation of hydroperoxides (SqOOH) generated by singlet oxygen reaction on squalene [see test 1 below]. Such an effect also opposes the intracellular oxidative stress induced by the "cis-UCA" production according to preliminary study results. Beyond this and with interest in the context of a desired innocuousness of reaction by-products, it is emphasized that this antioxidant power leads to oxidized forms of the thioether radical of the conjugates according to the invention, successively a sulfoxide and a sulfone, both of which are well tolerated by skin cells [see test 2 below];

an ability to improve dose-dependently the survival of epidermal cells (immortalized keratinocytes cell line called "HaCaT") exposed to UV-B cytotoxic doses, starting with the use of low concentrations in active substance [see test 3 below];

an ability to strongly absorb UV-B ultraviolet radiation like a filter, then to dissipate the absorbed energy by isomerization into a toxicity-free derivative [see test 4 below] and without the formation of an unwanted activity as it happens for instance with urocanic acid. Such a behavior is furthermore of enhanced interest when the photo-induced metabolite is a "nature-identical" compound due to the fact that it occurs naturally;

finally, the ability to oppose the photo-induced isomerization of trans-urocanic acid, which enables to ultimately limit the immunosuppressive effects of ultraviolet radiation [cf. test 5 below].

Regarding the state of the art and to the knowledge of the applicant, the prior art discloses a same photo-isomerization along with preservation of the activity of interest for benzylidene camphor derivatives used as ultraviolet filter in sun protection preparations (Beck I. et al., int. J. Cosmetic Science, 1981, vol. 3, pp. 139-152). These camphor derivatives are however structurally different from those which are the object of the present invention.

Concerning the inhibition of UV-induced conversion of trans-urocanic acid into immunosuppressant cis-urocanic acid, some agents advertised as "immunoprotective" are disclosed in the prior art, such as sulfonic-phenylbenzimidazole acids (Hurks H. M. H. et al., J. Invest. Dermatol., 1997, vol. 109, pp. 699-703), cinnamates, benzophenones and other dibenzoylmethanes (John J. Finlay-Jones et al., Mutation Res., 1998, vol. 422, pp. 155-159), etc. All of them are also structurally different from those which are the object of the present invention.

Moreover beyond these aspects, compounds of various interest that also bear a thiopropenamide unit are disclosed in the prior art (U.S. Pat. No. 5,464,832; EP 0410726; U.S. Pat. No. 5,300,672 and U.S. Pat. No. 3,914,301). In these documents, the targeted compounds however display distinctly antimicrobial, fungicidal, bactericidal and biocidal properties.

DETAILED DESCRIPTION OF THE INVENTION

The invention has therefore for first object a family of pure cis or (Z)-isomers conjugates obtained by a coupling reaction between (Z)-3-(alkylthio)propenoic acid and primary or secondary alkylamines or a selection of hydroxylated and non-ionizable polar amino acids, characterized in that said family is represented by the following general formula (I):

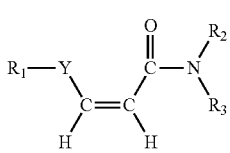

wherein:
- Y=S or SO;
- $R_1$ is a linear or branched $C_1$-$C_4$ alkyl group;
- $R_2$ is a hydrogen atom, or a linear or branched $C_1$-$C_4$ alkyl group;
- $R_3$ is:
  - a $C_1$-$C_{18}$ alkyl group, a $C_3$-$C_{18}$ alkene group, a $C_3$-$C_4$ alkyne group, said alkyl, alkene or alkyne groups being linear or branched and optionally substituted with a hydroxyl, a hydroxyphenyl or a dihydroxyphenyl group; or
  - the side chain of an amino acid chosen from tyrosine, hydroxyproline, serine and its homoserine and isoserine analogues, threonine and its homothreonine and isothreonine analogues.

The skilled person can easily identify the side chain of the above-mentioned amino acids. These amino acids are represented by one of the following formulae:

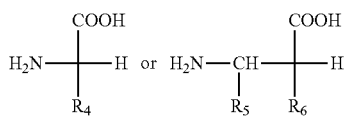

which correspond to tyrosine ($R_4$=4-hydroxyphenyl), serine ($R_4$=—$CH_2$—OH) and its homoserine ($R_4$=—$CH_2$—$CH_2$—OH) and isoserine ($R_5$=H, $R_6$=OH) analogues, threonine ($R_4$=—CH(OH)—$CH_3$) and its homothreonine ($R_4$=—$CH_2$—CH(OH)—$CH_3$) and isothreonine ($R_5$=$CH_3$, $R_6$=OH) analogues. These amino acids can also be defined by a registration number in a data bank (hydroxyproline, CAS n° 51-35-4).

According to a preferred embodiment of the invention, the (Z)-isomer conjugates of the invention are represented by the formula (II) here-below:

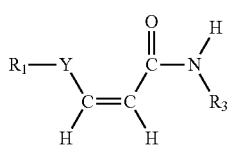

wherein:
- Y=S or SO;
- $R_1$ is a linear or branched $C_1$-$C_4$ alkyl group;
- $R_3$ is a $C_1$-$C_4$ alkyl group, a $C_3$-$C_4$ alkene group, a $C_3$-$C_4$ alkyne group, said alkyl, alkene or alkyne groups being linear or branched and optionally substituted with a hydroxyl, a hydroxyphenyl or a dihydroxyphenyl group.

Advantageously, the (Z)-isomer conjugates of formula (I) or (II) are as such that Y=S.

Advantageously, the (Z)-isomer conjugates of formula (I) or (II) are such that $R_1$ is a methyl group.

Advantageously, the (Z)-isomer conjugates of formula (I) or (II) are such that $R_3$ is an ethyl group substituted by a hydroxyl, a hydroxyphenyl or a dihydroxyphenyl group. Thus as an example of alkylamines involved in the coupling reaction with cis-3-methylthiopropenoic acid (Z-TMPA), ethanolamine, tyramine, a catecholamine like dopamine, adrenaline or noradrenaline, can be mentioned.

As non-exhaustive examples of (Z)-isomer conjugates of formula (I) or (II), the following compounds can be mentioned, the photo-isomerization-induced product (trans-isomer) of which naturally occurs in plants:
- (Z)—N-(2-hydroxyethyl)-3-(methylthio)propenamide
- (Z)—N-(4-hydroxyphenethyl)-3-(methylthio)propenamide.

To date and to the knowledge of the applicant, the (Z)-isomer conjugates of formula (I) are new with the exception of the 2-cis-entadamide A, isopenangin, N-ethyl-cis-3-butylmercaptoacrylamide and N-ethyl-cis-3-methylmercaptoacrylamide compounds.

The conjugates of formula (I) can be synthesized by the following production process developed by the applicant:
- i/ stereoselective preparation of (Z)-3-thiocyanatopropenoic acid by reaction of propiolic acid with potassium thiocyanate;
- ii/ alkylation reaction at low temperature of (Z)-3-thiocyanatopropenoic acid according to i/ using alkyl iodide, preferably methyl iodide, and then formation of the resulting (Z)-3-(alkylthio)propenoic acid synthon, preferably (Z)-3-methylthiopropenoic acid;
- iii/ coupling reaction at room temperature between (Z)-3-(alkylthio)propenoic acid according to ii/, preferably (Z)-3-methylthiopropenoic acid, and a primary or secondary alkylamine or a polar amino acid, preferably a linear or branched primary alkylamine, and even more preferably ethanolamine or tyramine, and formation of the resulting conjugated derivatives, preferably (Z)—N-(2-hydroxyethyl)-3-(methylthio)propenamide and (Z)—N-(4-hydroxyphenethyl)-3-(methylthio)propenamide. The coupling reaction is carried out with a coupling agent well-known to the skilled person, preferably N,N'-dicyclohexylcarbodiimide, and with a carboxylic function activator of the (Z)-3-alkylthiopropenoic acid synthon that is also well known to the skilled person, preferably hydroxybenzotriazole.

These (Z)-isomer conjugates are obtained in powdered solid form, are soluble in alcoholic medium, and are stable both in powder form and in solution over a period exceeding 28 days.

The above-mentioned conjugates (Z)—N-(2-hydroxyethyl)-3-(methylthio)propenamide and (Z)—N-(4-hydroxyphenethyl)-3-(methylthio)propenamide have the following physico-chemical and spectral characteristics:

(Z)—N-(2-hydroxyethyl)-3-(methylthio)propenamide

Rf=0.40 (CHCl$_3$/MeOH, 90:10);

m.p.=112° C.;

$^1$H NMR (CD$_3$OD): δ=2.32 ppm (s, 3H, CH$_3$), 3.31 (t, 2H, J=6 Hz, CH$_2$—NH), 3.60 ppm (t, 2H, J=6 Hz, CH$_2$—OH), 5.89 ppm (d, 1H, J=10 Hz, CH═), 6.93 ppm (d, 1H, J=10 Hz, CH═);

$^{13}$C NMR (CD$_3$OD): δ=19.2 ppm (CH$_3$), 42.8 ppm (N—CH$_2$), 61.8 ppm (CH$_2$—O), 115.9 ppm (═CH), 148.6 ppm (═CH—S), 169.2 ppm (C═O).

(Z)—N-(4-hydroxyphenethyl)-3-(methylthio)propenamide

Rf=0.35 (toluene/acetone/acetic acid, 100:50:2);

m.p.=132° C.;

$^1$H NMR (CD$_3$OD): δ=2.31 ppm (s, 3H, CH$_3$—S), 2.69 (t, 2H, J=7.5 Hz, CH$_2$-Ph), 3.35 ppm (t, 2H, J=7.5 Hz, CH$_2$—N), 5.83 ppm (d, 1H, J=10 Hz, CH═), 6.90 ppm (d, 1H, J=10 Hz, CH═), 6.70 ppm (d, 2H, J=8.5 Hz, C$_{Ph}$—H), 7.02 ppm (d, 2H, J=8.5 Hz, C$_{Ph}$—H); $^{13}$C NMR (CD$_3$OD): δ=19.2 ppm (CH$_3$—S), 35.9 ppm (CH$_2$-Ph), 42.2 ppm (CH$_2$—N), 116 ppm (CH═), 116.2 ppm (phenol), 130.7 ppm (phenol), 131.3 ppm (phenol), 148.4 ppm (═CH), 156.9 ppm (phenol), 169 ppm (C═O).

According to a second aspect, the invention also covers a composition for cosmetic or dermocosmetic use, intended for photoprotection, in particular of skin or appendages. This composition comprises as main active ingredient a compound of general formula (III) below in combination with any physiologically acceptable additive with skin or appendages:

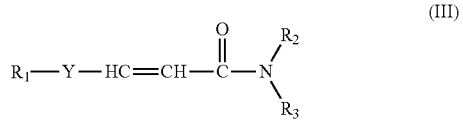

(III)

wherein:

Y, R$_1$, R$_2$ and R$_3$ are as defined here-above for the compounds of formula (I).

Advantageously, the cosmetic or dermocosmetic composition according to the invention comprises, as main active ingredient, a compound of general formula (IV):

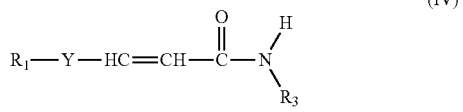

(IV)

wherein:

Y═S or SO;

R$_1$ is a linear or branched C$_1$-C$_4$ alkyl group;

R$_3$ is a linear or branched C$_1$-C$_4$ alkyl group, optionally substituted with a hydroxyl, a hydroxyphenyl or a dihydroxyphenyl group.

The general formula (III) includes both the Z-isomers of formula (IIIa), the E-isomers of formula (IIIb), and mixtures of these isomers, preferably the racemate:

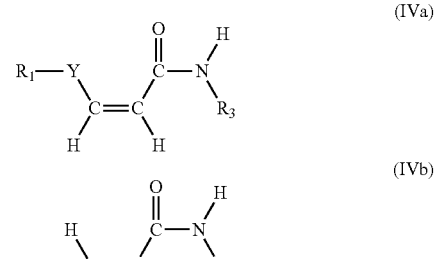

Similarly, the general formula (IV) includes both the Z-isomers of formula (IVa), the E-isomers of formula (IVb), and mixtures of these isomers, preferably the racemate:

In the context of the present invention, the term "main active ingredient" is intended to mean an active substance capable of opposing the harmful effects of sun radiation.

Advantageously, the amount of compound of general formula (III) or (IV) in the described compositions is in the range from 0.001% to 0.1% by weight based on the total weight of the composition, preferably from 0.005 to 0.05% % by weight.

The recommended molar concentration of the compound of general formula (III) or (IV) in the described compositions is advantageously in the range from 0.05 to 5 mM, preferably from 0.25 to 2.5 mM as in the illustrative tests hereafter.

Advantageously, the compound of general formula (III) or (IV) is such that Y═S.

Advantageously, the compound of general formula (III) or (IV) is such that R$_1$ is a methyl group.

Advantageously, the compound of general formula (III) or (IV) is such that R$_3$ is an ethyl group substituted by a hydroxyl, a hydroxyphenyl or a dihydroxyphenyl group.

Thus as an example of corresponding primary or secondary alkylamines involved in the coupling reaction with Z-TMPA and E-TMPA acids, mention can be made of ethanolamine, tyramine, a catecholamine like dopamine, adrenaline or noradrenaline.

Very particularly in the compositions according to the invention, the compound of general formula (III) or (IV) is respectively a (Z)-isomer conjugate of formula (IIIa) or (IVa) derived from (Z)-3-(alkylthio)propenoic acid.

Most preferably, the compositions according to the invention comprise, as main ingredient, (Z)—N-(2-hydroxyethyl)-3-(methylthio)propenamide or (Z)—N-(4-hydroxyphenethyl)-3-(methylthio)propenamide.

The compositions according to the invention are suitable for topical cutaneous administration, presented under all forms normally used for such an administration. By way of non-limiting information, compositions can be in the form of suspensions, lotions, creams, aqueous or hydroalcoholic gels, powders and various emulsions that can be possibly microemulsions or nanoemulsions, etc.

The compositions according to the invention can contain as physiologically acceptable additive at least one additive known by the skilled person and compatible in cosmetic or dermocosmetic areas, chosen among oils, waxes, silicone elastomers, surfactants, co-surfactants, thickeners and/or gellants, humectants, emollients, organic or inorganic sun filters, photostabilizing agents, preservatives with the exception of aldehyde donor preservatives, dyes, matifying agents, tensors, sequestering agents, perfumes, etc, and mixtures thereof.

Said organic or inorganic sun filters are active in the UV-A and/or UV-B, and are chosen among anthranilates, cinnamic derivatives, dibenzoylmethane derivatives, salicylic derivatives, camphor derivatives, triazine derivatives, benzophenone derivatives, beta,beta-diphenylacrylate derivatives, benzotriazole derivatives, benzalmalonate derivatives, benzimidazole derivatives, imidazolines, bis-benzoazolyl derivatives, benzoxazole derivatives, p-aminobenzoic acid (PABA) derivatives, methylene bis-(hydroxyphenyl benzotriazole) derivatives, filter polymers, filter silicones, dimers derived from alpha-alkylstyrene, 4,4-diarylbutadienes, metal oxide pigments or nanopigments (titanium, zinc, iron, zirconium and cerium oxides), coated or uncoated, and mixtures thereof.

The compositions according to the invention can further comprise one or several additional active ingredients, the skilled person however ensuring that the possible additional active compounds as well as their proportions are chosen in such a way that the advantageous properties acknowledged for the compositions according to the invention are not affected. These additional active ingredients can be chosen, without the list being limited, among deglycation agents, agents that increase the synthesis of collagen or elastin or prevent their degradation, agents that increase the synthesis of glycosaminoglycans or proteoglycans or prevent their degradation, agents that increase cell proliferation, depigmenting or pro-pigmenting agents, antioxidant or anti-radical or anti-pollution agents, moisturizing agents, agents that stimulate lipolysis, draining or detoxifying agents, anti-inflammatory agents, penetration enhancer agents, desquamative agents, soothing and/or anti-irritating agents, astringent agents, agents that act on the microcirculation, etc, and mixtures thereof.

The compositions according to the invention can also further comprise at least a skin tanning and/or browning agent.

Another object of the invention relates to the use, in a cosmetic or dermocosmetic composition, of a compound of formula (III) or (IV) such as previously defined, as a photoprotective agent against sun radiation.

Another object of the invention relates to a method of photoprotection against sun radiation which comprises the application of a cosmetic or dermocosmetic composition such as previously defined and containing a compound of formula (III) or (IV). In one embodiment the method comprises topically applying the cosmetic or dermocosmetic composition of the invention to skin.

Preferably in the above-mentioned use and method, the compound of formula (III) or (IV) is respectively a (Z)-isomer conjugate of formula (IIIa) or (IVa) derived from (Z)-3-(alkylthio)propenoic acid, especially (Z)—N-(2-hydroxyethyl)-3-(methylthio)propenamide or (Z)—N-(4-hydroxyphenethyl)-3-(methylthio)propenamide.

EXAMPLES

Example 1

For illustrative purposes, four formulation examples of composition according to the invention are mentioned hereafter, containing a conjugate derived from cis-3-methylthiopropenoic acid of the above-mentioned general formula (I):

| Formula A (cream) | |
|---|---|
| (Z)-N-(2-hydroxyethyl)-3-(methylthio)propenamide | 0.008% |
| Hydrogenated polyisobutene | 7% |
| Isobutyl myristate | 7% |
| Cetyl palmitate | 7% |
| Ethylene glycol monostearate | 5% |
| Sorbitan laurate | 2% |
| Polysorbate 20 | 2% |
| Carbomer (acrylate/acrylamide copolymer & mineral oil) | 0.3% |
| Phenoxyethanol | 0.5% |
| Water | qsp 100% |

| Formula B (gel) | |
|---|---|
| (Z)-N-(4-hydroxyphenethyl)-3-(methylthio)propenamide | 0.011% |
| Carbomer (acrylate/acrylamide copolymer & mineral oil) | 1.5% |
| Sodium benzoate | 0.2% |
| Sorbic acid | 1% |
| 1,3-butanediol | 10% |
| Glycerin | 5% |
| Sodium hydroxide | 0.13% |
| Phenoxyethanol | 0.9% |
| Water | qsp 100% |

| Formula C (lotion) | |
|---|---|
| (E)-N-(4-hydroxyphenethyl)-3-(methylthio)propenamide | 0.031% |
| Chlorphenesin | 0.2% |
| Phenonip (parabens - butyl, ethyl, isobutyl, methyl, propyl parahydroxybenzoates, and phenoxyethanol) | 0.6% |
| Xamhan gum | 0.3% |
| Glycerin | 2.5% |
| Triethanolamine | 0.03% |
| Water | qsp 100% |

| Formula D (emulsion) | |
|---|---|
| (Z)-N-(2-hydroxyethyl)-3-(methylthio)propenamide | 0.018% |
| Hydrogenated polydecene | 8% |
| Capric/caprylic triglycerides | 2% |
| Ethoxydiglycol oleate | 8% |
| Glyceryl stearate | 2% |
| Dimethicone | 1% |
| Polyethylene glycol-100 stearate and glyceryl stearate | 5% |
| Propyl paraben | 0.3% |
| Stearyl alcohol | 1% |
| EDTA (ethylene diamine disodium salt dihydrate acid tetraacetic acid) | 0.2% |

-continued

| Formula D (emulsion) | |
|---|---|
| Glycerin | 3% |
| Xanthan gum | 0.4% |
| Wheat germ oil | 1% |
| *Macadamia* seed oil | 1% |
| Polyethylene glycol-8 & tocopherol & ascorbyl palmitate & ascorbic acid & citric acid | 0.07% |
| Triethanolamine | 0.35% |
| Water | qsp 100% |

(In all the examples the % are % by weight).

Example 2

Merely by way of information, the invention is hereafter illustrated by the following tests which are mentioned above in the description of the invention (tests 1 to 5).

Test 1: Evidence of the Antioxidant Potential of the Compounds of Formula (IIIc) and (IIIb) Against Squalene Hydroperoxidation by Singlet Oxygen Principle: the aim is to demonstrate a possible scavenging effect ("quenching") of the compounds according to the invention on squalene hydroperoxides generated by the action of dissolved molecular oxygen on squalene in the presence of a photosensitizing agent (methylene blue).

Experimentally, a squalene solution at 5 g/100 mL, a methylene blue solution at 5 mM and a solution of the compound according to the invention (from 1 to 5 mM) or a control compound (methylthiopropylamido acetyl methionine-AMDM) were prepared after being dissolved in 100 mL of methanol (HPLC grade). Then in a UV-B oven, each solution was poured in equal parts into an uncovered Petri dish, in order to be submitted to a radiation dose (1D) of 1.42 J·cm$^{-2}$. At the end of the radiation, volumes of the solutions were recovered, adjusted to 20 mL with methanol prior to analysis by HPLC assay and after removal of methylene blue. The "quenching," rate was then deduced from the following equation:

$$\% \text{ protection} = \frac{\text{amount of oxidized squalene (control)} - \text{amount of oxidized squalene (test)}}{\text{amount of oxidized squalene (control)} \times 100}$$

The results are gathered in table 1 below:

TABLE 1

| Compound | % squalene protection |
|---|---|
| Control (AMDM, 1 mM) | 3 |
| Control (AMDM, 5 mM) | 15 |
| (Z)-N-(2-hydroxyethyl)-3-(methylthio)propenamide (1 mM) | 24 |
| (Z)-N-(2-hydroxyethyl)-3-(methylthio)propenamide (5 mM) | 25 |
| (Z)-N-(4-hydroxyphenethyl)-3-(methylthio)propenamide (1 mM) | 35 |
| (Z)-N-(4-hydroxyphenethyl)-3-(methylthio)propenamide (5 mM) | 44 |
| (E)-N-(2-hydroxyethyl)-3-(methylthio)propenamide (1 mM) | 71 |
| (E)-N-(4-hydroxyphenethyl)-3-(methylthio)propenamide (1 mM) | 30 |

The results in table 1 show that the compounds according to the invention are capable of opposing efficiently the photo-induced oxidation of squalene into hydroperoxides.

Test 2: Evidence of the Absence of Cytotoxic Potential of the Oxidation by-Products of the (Z)-Isomer Conjugates of Formula (I)

Experimentally, the test was carried out on a cell line of immortalized keratinocytes "HaCaT" maintained by subculture in a complete culture medium "DMEM" (with 10% foetal calf serum) in a humid atmosphere at 37° C. and 5% $CO_2$. HaCaT cells were seeded in 24-well plates at the rate of $1·10^5$ cells per well.

Sulfoxide and sulfone derivatives of (Z)-isomer conjugates of formula (I) were synthesized after a stoichiometric exposure to hydrogen peroxide ($H_2O_2$), then purified and finally quantified.

500 µl of sulfoxide and sulfone oxidation by-products from the conjugates according to the invention were added in each well, at the concentration of 2.5 mM in PBS. After removal of the medium, the HaCaT keratinocytes cell viability was measured using the "MTT method" (MTT standing for (4,5-dimethylthiazol-2-yl)-2,5-diphenyltetrazolium bromide) (solution at 500 µg/ml) and by spectrophotometry (absorbance at 550 nm). Expressed as the average values obtained from three independent experiments, the results are gathered in table 2 below, in comparison with those obtained for the non-irradiated cells.

TABLE 2

| Compound | % cell viability |
|---|---|
| Control (non-irradiated cells) | 100 |
| (Z)-N-(2-hydroxyethyl)-3-(methylthiosulfinyl)propenamide (2.5 mM) | 94.3 |
| (Z)-N-(2-hydroxyethyl)-3-(methylthiosulfonyl)propenamide (2.5 mM) | 93.1 |
| (Z)-N-(4-hydroxyphenethyl)-3-(methylthiosulfinyl)propenamide (2.5 mM) | 95.6 |
| (Z)-N-(4-hydroxyphenethyl)-3-(methylthiosulfonyl)propenamide (2.5 mM) | 95.0 |

The results in table 2 show the absence of toxicity of the oxidation by-products of the (Z)-isomer conjugates of formula (I).

Test 3: Evidence of the Ability of the (Z)-Isomer Conjugates of Formula (I) to Make Viable a Keratinocyte Cell Line Exposed to UV-B Cytotoxic Doses Experimentally, the study was also carried out on a cell line of immortalized keratinocytes "HaCaT" seeded in 24-well plates at a rate of 8000 cells per square centimeter, namely 15200 cells per welkin 0.5 ml culture medium (with 10% foetal calf serum).

500 µl of the conjugate according to the invention were added in each well at a concentration from 0.05 to 0.5 mM in PBS. The cells in the presence of active ingredient were then exposed to ultraviolet radiations (UV-B) at the moderate dose of 100 mJ·cm–$^2$, and then placed into a medium without active ingredient for 24 hours. After removal of the medium, the HaCaT keratinocytes cell viability was also measured using the "MTT method" (solution at 250 µg/ml) and by spectrophotometry (absorbance at 570 nm). Gathering the average values obtained from three independent experiments, the results are presented in table 3 below, in comparison with those obtained for two controls, the non-irradiated cells and the non-treated irradiated cells with the conjugates according to the invention.

TABLE 3

| Compound | % cell viability |
|---|---|
| Control (non-irradiated cells) | 100 |
| Control + UV-B irradiation = 100 mJ/cm² | 46 |
| (Z)-N-(2-hydroxyethyl)-3-(methylthio)propenamide (0.1 mM) | 64 |
| (Z)-N-(2-hydroxyethyl)-3-(methylthio)propenamide (0.25 mM) | 85 |
| (Z)-N-(2-hydroxyethyl)-3-(methylthio)propenamide (0.5 mM) | 94 |
| (Z)-N-(4-hydroxyphenethyl)-3-(methylthio)propenamide (0.1 mM) | 70 |
| (Z)-N-(4-hydroxyphenethyl)-3-(methylthio)propenamide (0.25 mM) | 93 |
| (Z)-N-(4-hydroxyphenethyl)-3-(methylthio)propenamide (0.5 mM) | 100 |
| (Z)-N-ethyl-3-(methylthio)propenamide (0.5 mM) | 86 |

The results in table 3 show a dose-dependent cell viability for the compounds according to the invention, with a keratinocyte photoprotection starting at 0.1 mM and with a complete or nearly complete photoprotection at 0.5 mM.

Test 4: Evidence of the Ability of the (Z)-Isomer Conjugates of Formula (I) to Absorb Ultraviolet Radiation by Photo-Isomerization Principle: the aim is to check whether the conjugates according to the invention are able to isomerize under UV-B irradiation.

Experimentally, 2 ml of a squalene solution at 5 g/100 mL and 2 mL of a solution of compound according to the invention at the concentration of 25 mM in methanol were introduced into a 20 mL measuring cylinder, and then supplemented with methanol up to 20 mL. The preparation thus obtained was poured into a Petri dish onto which an irradiation dose of 1 J·cm⁻² was applied in a UV-B oven. At the end of the irradiation, the solutions were collected and analyzed by HPLC dosage. Volumes were previously standardized with methanol.

Chromatographic profiles were thus obtained, and the formation of the E-isomer was investigated. An isomerization rate was then determined by comparison with a control profile. The results obtained are gathered in table 4 below:

TABLE 4

| Compound | % isomerization |
|---|---|
| (Z)-N-(2-hydroxyethyl)-3-(methylthio)propenamide (2.5 mM) | 62 |
| (Z)-N-(4-hydroxyphenethyl)-3-(methylthio)propenamide (2.5 mM) | 95 |
| (Z)-N-ethyl-3-(methylthio)propenamide (2.5 mM) | 60 |
| (Z)-N-(2-hydroxyethyl)-3-(methylthiosulfinyl)propenamide (2.5 mM) | 64 |

The results in table 4 show that the compounds according to the invention are capable of absorbing radiation efficiently due to the production of their trans-configuration stereoisomer.

Test 5: Evidence of the Ability of the (Z)-Isomer Conjugates of Formula (I) to Oppose the Trans-Urocanic Acid Photo-Induced Isomerization Principle: the aim is to check whether the conjugates according to the invention are capable of opposing the trans-urocanic acid photo-isomerization.

Experimentally, the study was carried out almost identically as in tests 1 and 4 above. Beforehand, it was checked that under defined experimental conditions, trans-urocanic acid generates a significant amount of cis-urocanic acid that can be measured by HPLC analysis. The irradiation dose (1D) was 31 mJ·cm⁻² for a compound concentration of 5 mM. The results are gathered in table 5 below:

TABLE 5

| Compound | % inhibition of (E)-urocanic acid |
|---|---|
| (Z)-N-(2-hydroxyethyl)-3-(methylthio)propenamide (5 mM) | 75 |
| (Z)-N-(4-hydroxyphenethyl)-3-(methylthio)propenamide (5 mM) | 78 |

The results in table 5 show that the compounds according to the invention are efficient at a low or moderate dose to protect trans-urocanic acid against UV-B irradiation.

What is claimed is:

1. A compound represented by the following general formula (I):

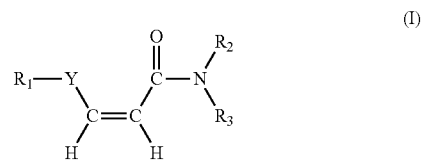

wherein:
Y=S or SO;
$R_1$ is a linear or branched $C_1$-$C_4$ alkyl group;
$R_2$ is a hydrogen atom, or a linear or branched $C_1$-$C_4$ alkyl group;
$R_3$ is:
a $C_1$-$C_{18}$ alkyl group, a $C_3$-$C_{18}$ alkene group, or a $C_3$-$C_4$ alkyne group, said alkyl, alkene and alkyne groups being linear or branched and optionally substituted with a hydroxyl, a hydroxyphenyl or a dihydroxyphenyl group; or
the side chain of an amino acid selected from the group consisting of tyrosine, hydroxyproline, serine, homoserine, isoserine, threonine, homothreonine and isothreonine;
provided that said compound is not one of the following compounds: 2-cis-entadamide A, isopenangin, N-ethyl-cis-3-butylmercaptoacrylamide and N-ethyl-cis-3-methylmercaptoacrylamide.

2. The compound according to claim 1, represented by the following general formula (II):

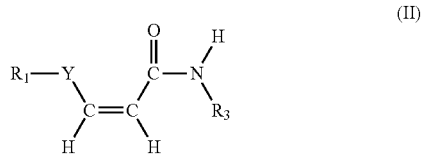

wherein:
Y=S or SO;
$R_1$ is a linear or branched $C_1$-$C_4$ alkyl group;
$R_3$ is a $C_1$-$C_4$ alkyl group, a $C_3$-$C_4$ alkene group, or a $C_3$-$C_4$ alkyne group, said alkyl, alkene and alkyne groups being linear or branched and optionally substituted with a hydroxyl, a hydroxyphenyl or dihydroxyphenyl group.

3. The compound according to claim 1, wherein Y is S.

4. The compound according to claim 1, wherein $R_1$ is a methyl group.

5. The compound according to claim 1, wherein $R_3$ is an ethyl group substituted by a hydroxyl, a hydroxyphenyl or a dihydroxyphenyl group.

6. The compound according to claim 1, which is (Z)—N-(4-hydroxyphenethyl)-3-(methylthio)propenamide.

7. A cosmetic or dermocosmetic composition useful for photoprotection, which comprises as main active ingredient a compound of formula (IIIa), a compound of formula (IIIb), or a mixture thereof, in combination with any additive physiologically compatible with skin or appendages:

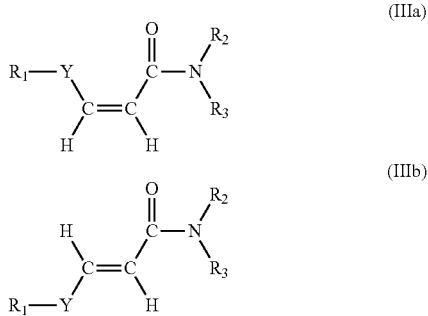

wherein:
Y=S or SO;
$R_1$ is a linear or branched $C_1$-$C_4$ alkyl group;
$R_2$ is a hydrogen atom, or a linear or branched $C_1$-$C_4$ alkyl group;
$R_3$ is:
  a $C_1$-$C_{18}$ alkyl group, a $C_3$-$C_{18}$ alkene group, or a $C_3$-$C_4$ alkyne group, said alkyl, alkene or alkyne groups being linear or branched and optionally substituted with a hydroxyl, a hydroxyphenyl or a dihydroxyphenyl group; or
  the side chain of an amino acid selected from the group consisting of tyrosine, hydroxyproline, serine, homoserine, isoserine, threonine, homothreonine and isothreonine; and
wherein the amount of main active ingredient is in the range from 0.001% to 0.1% by weight based on the total weight of the composition.

8. The cosmetic or dermocosmetic composition according to claim 7, which comprises, as main active ingredient, a compound of formula (IVa), a compound of formula (IVb), or a mixture thereof:

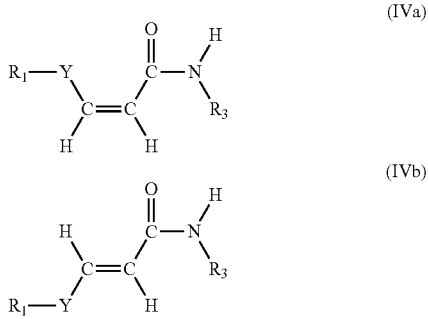

wherein:
Y=S or SO;
$R_1$ is a linear or branched $C_1$-$C_4$ alkyl group;
$R_3$ is a linear or branched $C_1$-$C_4$ alkyl group optionally substituted with a hydroxyl, a hydroxyphenyl or a dihydroxyphenyl group.

9. The cosmetic or dermocosmetic composition according to claim 7, wherein in the compound of formula (IIIA) or (IIIb) Y is S, $R_1$ is a methyl group and $R_3$ is an ethyl group substituted by a hydroxyl, a hydroxyphenyl or a dihydroxyphenyl group.

10. The cosmetic or dermocosmetic composition according to claim 7, wherein the main active ingredient is (Z)—N-(2-hydroxyethyl)-3-(methylthio)propenamide or (Z)—N-(4-hydroxyphenethyl)-3-(methylthio)propenamide.

11. The cosmetic or dermocosmetic composition according to claim 7, which further comprises an organic or inorganic sun filter that is active in the UV-A and/or UV-B, selected from the group consisting of: anthranilates, cinnamic derivatives, dibenzoylmethane derivatives, salicylic derivatives, camphor derivatives, triazine derivatives, benzophenone derivatives, beta,beta-diphenylacrylate derivatives, benzotriazole derivatives, benzalmalonate derivatives, benzimidazole derivatives, imidazolines, bis-benzoazolyl derivatives, benzoxazole derivatives, p-aminobenzoic acid (PABA) derivatives, methylene bis-(hydroxyphenyl benzotriazole) derivatives, filter polymers, filter silicones, dimers derived from alpha-alkylstyrene, 4,4-diarylbutadienes, metal oxide pigments or nanopigments, coated or uncoated, and mixtures thereof.

12. The cosmetic or dermocosmetic composition according to claim 7, which further comprises one or several active ingredients selected from the group consisting of: deglycation agents, agents that increase the synthesis of collagen or elastin or prevent their degradation, agents that increase the synthesis of glycosaminoglycans or proteoglycans or prevent their degradation, agents that increase the cell proliferation, depigmenting or pro-pigmenting agents, antioxidant or anti-radical or anti-pollution agents, moisturizing agents, agents that stimulate lipolysis, draining or detoxifying agents, anti-inflammatory agents, penetration enhancer agents, desquamative agents, soothing and/or anti-irritating agents, astringent agents, agents that act on the microcirculation, and mixtures thereof.

13. A method of photoprotection against sun radiation, which comprises applying to skin a cosmetic or dermocosmetic composition comprising, as main active ingredient, a compound of formula (IIIa), a compound of formula (IIIb), or a mixture thereof, in combination with any additive physiologically compatible with skin or appendages:

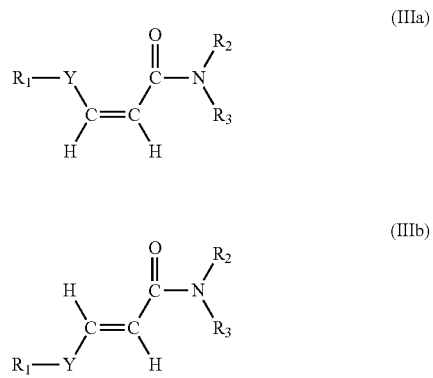

wherein:
Y=S or SO;
$R_1$ is a linear or branched $C_1$-$C_4$ alkyl group;
$R_2$ is a hydrogen atom, or a linear or branched $C_1$-$C_4$ alkyl group;
$R_3$ is:
- a $C_1$-$C_{18}$ alkyl group, a $C_3$-$C_{18}$ alkene group, or a $C_3$-$C_4$ alkyne group, said alkyl, alkene or alkyne groups being linear or branched and optionally substituted with a hydroxyl, a hydroxyphenyl or a dihydroxyphenyl group; or
- the side chain of an amino acid selected from the group consisting of tyrosine, hydroxyproline, serine, homoserine, isoserine, threonine, homothreonine and isothreonine.

14. The method according to claim 13, which comprises applying to skin a cosmetic or dermocosmetic composition comprising, as main active ingredient, a compound of formula (IVa), a compound of formula (IVb), or a mixture thereof in combination with any additive physiologically compatible with skin or appendages:

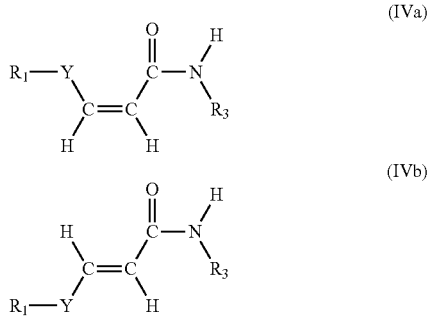

wherein:
Y=S or SO;
$R_1$ is a linear or branched $C_1$-$C_4$ alkyl group;
$R_3$ is a linear or branched $C_1$-$C_4$ alkyl group optionally substituted with a hydroxyl, a hydroxyphenyl or a dihydroxyphenyl group.

15. The method according to claim 13, wherein in the compound of formula (IIIa) or (IIIb) Y is S, $R_1$ is a methyl group and $R_3$ is an ethyl group substituted by a hydroxyl, a hydroxyphenyl or a dihydroxyphenyl group.

16. The method according to claim 13, wherein the main active ingredient is (Z)—N-(2-hydroxyethyl)-3-(methylthio)propenamide or (Z)—N-(4-hydroxyphenethyl)-3-(methylthio)propenamide.

17. The method according claim 13, wherein the cosmetic or dermocosmetic composition comprises from 0.001% to 0.1% by weight of main active ingredient based on the total weight of the composition.

18. The method according to claim 13, wherein the cosmetic or dermocosmetic composition further comprises an organic or inorganic sun filter that is active in the UV-A and/or UV-B, selected from the group consisting of: anthranilates, cinnamic derivatives, dibenzoylmethane derivatives, salicylic derivatives, camphor derivatives, triazine derivatives, benzophenone derivatives, beta,beta-diphenylacrylate derivatives, benzotriazole derivatives, benzalmalonate derivatives, benzimidazole derivatives, imidazolines, bisbenzoazolyl derivatives, benzoxazole derivatives, p-aminobenzoic acid (PABA) derivatives, methylene bis-(hydroxyphenyl benzotriazole) derivatives, filter polymers, filter silicones, dimers derived from alpha-alkylstyrene, 4,4-diarylbutadienes, metal oxide pigments or nanopigments, coated or uncoated, and mixtures thereof.

19. The method according to claim 13, wherein the cosmetic or dermocosmetic composition further comprises one or several active ingredients selected from the group consisting of: deglycation agents, agents that increase the synthesis of collagen or elastin or prevent their degradation, agents that increase the synthesis of glycosaminoglycans or proteoglycans or prevent their degradation, agents that increase the cell proliferation, depigmenting or pro-pigmenting agents, antioxidant or anti-radical or anti-pollution agents, moisturizing agents, agents that stimulate lipolysis, draining or detoxifying agents, anti-inflammatory agents, penetration enhancer agents, desquamative agents, soothing and/or anti-irritating agents, astringent agents, agents that act on the microcirculation, and mixtures thereof.

* * * * *